(12) United States Patent
Gevaert et al.

(10) Patent No.: US 10,117,643 B2
(45) Date of Patent: Nov. 6, 2018

(54) CREATED CAVITY TEMPERATURE SENSOR

(71) Applicants: Theresa Anne Gevaert, Greenville, SC (US); Matthew Raymond Gevaert, Greenville, SC (US)

(72) Inventors: Theresa Anne Gevaert, Greenville, SC (US); Matthew Raymond Gevaert, Greenville, SC (US)

( * ) Notice: Subject to any disclaimer, the term of this patent is extended or adjusted under 35 U.S.C. 154(b) by 0 days.

(21) Appl. No.: 14/696,395

(22) Filed: Apr. 25, 2015

(65) Prior Publication Data

US 2016/0310112 A1    Oct. 27, 2016

(51) Int. Cl.
*A61B 5/00* (2006.01)
*A61B 10/00* (2006.01)
*A61B 5/01* (2006.01)

(52) U.S. Cl.
CPC ........ *A61B 10/0012* (2013.01); *A61B 5/0022* (2013.01); *A61B 5/01* (2013.01); *A61B 5/6816* (2013.01); *A61B 5/002* (2013.01); *A61B 2010/0019* (2013.01)

(58) Field of Classification Search
CPC ......... A61B 5/01; A61B 5/015; G01K 13/002
USPC ....................................................... 600/549
See application file for complete search history.

(56) References Cited

U.S. PATENT DOCUMENTS

| | | | | |
|---|---|---|---|---|
| 3,604,266 A * | 9/1971 | Chilton | ................. | G01K 13/002 116/294 |
| 6,862,550 B1 * | 3/2005 | Cook | .................. | G01K 13/002 374/45 |
| 2003/0234726 A1 * | 12/2003 | Chen | .................... | A61B 5/0008 340/573.1 |
| 2004/0123625 A1 * | 7/2004 | Waldman | ........... | A44C 15/0035 63/12 |
| 2004/0242976 A1 * | 12/2004 | Abreu | .................. | A61B 5/0008 600/315 |
| 2007/0006494 A1 * | 1/2007 | Hayes | .................. | A01K 11/004 40/301 |

(Continued)

FOREIGN PATENT DOCUMENTS

WO    WO 2004027363 A1 *    4/2004    ............... G01K 1/02

OTHER PUBLICATIONS

International Search Report dated Jul. 28, 2015 in counterpart patent application PCT/US2015/027677.

(Continued)

*Primary Examiner* — Daniel Cerioni
(74) *Attorney, Agent, or Firm* — Smith Moore Leatherwood LLP; Thomas W. Epting (57) ABSTRACT

With the Quantified Self movement becoming prevalent, more people are looking to incorporate technology to acquire data regarding aspects of a person's daily life in terms of inputs (e.g. food consumed, quality of surrounding air), states (e.g. blood oxygen levels, body temperature), and/or performance. This self-monitoring concept combines wearable sensors with computing devices to produce an output to improve daily functioning. Disclosed is a device that senses and measures the created cavity temperature (CCT) within an artificial cavity in the wearer's body. This current device provides a wearable thermometer that measures temperature for a convenient, comfortable method of continuously tracking the wearer's temperature.

8 Claims, 7 Drawing Sheets

(56) References Cited

U.S. PATENT DOCUMENTS

| | | | |
|---|---|---|---|
| 2007/0160112 A1* | 7/2007 | Nanda | G01K 1/028 374/163 |
| 2008/0146890 A1 | 6/2008 | Leboeuf et al. | |
| 2009/0241599 A1* | 10/2009 | Stanke | A44C 7/002 63/13 |
| 2010/0217099 A1* | 8/2010 | LeBoeuf | A61B 5/00 600/301 |
| 2011/0224493 A1* | 9/2011 | Oyadiran | A61B 1/00016 600/200 |
| 2011/0257521 A1 | 10/2011 | Fraden | |
| 2013/0023772 A1* | 1/2013 | Kinsley | A61B 5/01 600/474 |
| 2013/0054150 A1 | 2/2013 | Sacks et al. | |
| 2013/0234726 A1 | 9/2013 | Hobelsberger | |
| 2013/0310658 A1 | 11/2013 | Ricks et al. | |
| 2013/0310704 A1 | 11/2013 | James et al. | |
| 2014/0051948 A1 | 2/2014 | Leboeuf et al. | |
| 2014/0206976 A1* | 7/2014 | Thompson | A61B 5/0006 600/391 |
| 2015/0351690 A1* | 12/2015 | Toth | A61B 5/6833 600/373 |
| 2016/0213354 A1* | 7/2016 | Levin | A61B 5/7275 |

OTHER PUBLICATIONS

Written Opinion of the International Searching Authority dated Jul. 28, 2015 in counterpart patent application PCT/US2015/027677.
European Opinion and Search Report dated Sep. 18, 2017 in counterpart European Patent Application No. 15783074.6.

* cited by examiner

CREATED CAVITY TEMPERATURE SENSOR

RELATED APPLICATIONS

This application claims priority to U.S. Provisional Application Ser. No. 61/984,732, which was filed on Apr. 26, 2014.

BACKGROUND OF THE INVENTION

The Quantified Self is a movement to incorporate technology to improve daily function by use of self-tracking data. With the Quantified Self movement becoming prevalent, more people are looking to incorporate technology acquire data regarding aspects of a person's daily life in terms of inputs (e.g. food consumed, quality of surrounding air), states (e.g. blood oxygen levels, body temperature), and/or performance. This self-monitoring concept combines wearable sensors with computing devices to produce an output to improve daily functioning.

Many thermometers are currently available for measuring a wearer's internal body temperature at a given time, after which they are removed. However, most of them do not offer a convenient way of measuring temperature over a time interval due to their bulky size and/or uncomfortable design. The sensing devices that are commercially available measure temperature through a naturally enclosed cavity (e.g. ear canal, armpit, vagina, rectum, and mouth), see, US Patent Application Publication US2002/0068877 to Abramoritch, US Patent Application Publication US2005/0281314 to Fraden, and US Patent Application Publication US2012/0238900 to Rechberg or skin, see, US Patent Application Publication US2011/0158284 to Goto and U.S. Pat. No. 7,787,973 to Pompei. The natural cavity provides a measure of the body's internal temperature.

An exemplary technology lag area with these thermometers has been shown through their lack of convenience and comfort. Many at home products require manual temperature measuring; therefore, continuous or periodic temperature monitoring is troublesome and most times unattainable. A wearable thermometer that accurately measures small changes in useful temperature is needed to acquire information about the wearer's physiological state (e.g. fever, stress, menstrual cycle). Also, a bulky sensor design is common for the current temperature monitors, with size and/or discomfort not permitting a person to wear the device during daily activities or sleeping for continuous temperature measurements.

As such, the development of a wearable device for measuring the wearer's accurate useful temperature during daily activities or sleeping is needed in the field. Further, a thermometer that offers constant monitoring through a convenient at-home device is desired. This will advance the Quantified Self movement by offering a controllable, self-tracking method for determination of fever, stress and/or fertility. Additionally, this advancement will benefit the field with a reduction in medical cost by eliminating excess doctor visits and providing a natural method to determine fertility compared to medicine.

SUMMARY

In one specific embodiment, the present invention provides a device for measuring a useful temperature through an artificial created cavity, meaning a cavity in the device wearer's body that is not a result of natural anatomy, this temperature also known as created cavity temperature (CCT). The CCT is distinctly different than a person's internal body temperature (IBT) and surface body temperature (SBT), where the temperature inside the created cavity does not need to correlate on a relationship basis with IBT and/or SBT. In one non-limiting example, the disclosed device is similar to an earring, which can be worn during sleep to monitor a woman's fertility trends, where the created cavity was the result of an ear piercing procedure. In this example, the device is inserted into the created cavity through the two holes, an entrance and exit, originally formed by the piercing procedure. In another non-limited example, the device may be similar to a belly button ring.

A second embodiment, the device also comprises a temperature sensor, which can be positioned, for example and without limitation, within and/or through the created cavity. The sensor operates periodically or constantly through a specific time interval and reads temperature periodically or constantly.

In another embodiment, the temperature measuring device contains a miniaturized transmitter with optional wireless communication components. To power these components, some require batteries and some do not.

According to one embodiment, the device partially or completely closes the gap at the two or more cavity openings through which the device was inserted into the created cavity. This closure may serve to physically affix the device in the created cavity. An example of such a closure is similar to an earring backing in which the backing of the earring affixes the earring to the ear when assembled. According to another embodiment, the means of closure includes an insulating component that more stably maintains the temperature inside the created cavity.

In a further embodiment, the device encompasses miniaturized low power rechargeable battery components to provide power to the system.

In another embodiment, the transmitter has no battery source and receives power through harvesting the energy from Wi-Fi and other signals for device communication.

The current system utilizes an artificially created physiologic cavity, in which the temperature measurement is regulated by CCT. This created cavity does not exist within the natural body. The device can be assembled so as to partially or completely close the artificially created cavity.

The system can also be capable of incorporating a small, compact, lightweight design, for example using soft or flexible materials, increasing the comfort and ease for wearing at home during sleep.

It is contemplated that, in operation, the system is used for measurement of CCT, with information available for tracking and/or deriving medical useful information and determining fertility, fever, sickness or constant temperature monitoring system for hospital use.

BRIEF DESCRIPTION OF THE DRAWINGS

A full and enabling disclosure, including the best mode thereof, to one of ordinary skill in the art, is set forth more particularly in the remainder of the specification, including reference to the accompanying Figures. The Figures illustrate certain aspects of the current invention and together with the description, serve to explain, without limitation, the principles of the invention. Like reference characters used therein indicate like parts throughout the several drawings.

DETAILED DESCRIPTION

Reference will now be made in detail to various embodiments of the presently disclosed subject matter, one or more examples of which are set forth below. Each embodiment is provided by way of explanation, not limitation, of the subject matter. In fact, it will be apparent to those skilled in the art that various modifications and variations may be made to the present disclosure without departing from the scope or spirit of the disclosure. For instance, features illustrated or described as part of one embodiment may be used in another embodiment to yield a still further embodiment. Thus, it is intended that the present disclosure cover such modifications and variations as come within the scope of the appended claims and their equivalents.

Ranges can be expressed herein as from "about" one particular value, and/or to "about" another particular value. When such a range is expressed, another aspect comprises from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description comprises instances where said event or circumstance occurs and instances where it does not.

The present disclosure is generally directed towards a device to measure a useful body temperature. More specifically, the device measures the created cavity temperature (CCT) within an artificial created cavity in living tissue or the wearer's body into which the device is inserted. This current device provides a wearable thermometer that continuously or periodically measures temperature for a convenient, comfortable method of continuously tracking the wearer's temperature.

CCT are measurements only available from an artificially created cavity in the wearer's body, where the created cavity is formed artificially, as in a non-limiting example, an earring piercing procedure. The disclosed device measures CCT within the created cavity to track the wearer's useful temperature. The aspects of the created cavity are further described below. CCT is not the same temperature measurement as core body temperature (CBT), internal body temperature (IBT), basal body temperature (BBT) body cavity temperature (BCT), and/or surface body temperature (SBT). This is recognized by reason that the temperature inside the created cavity does not need to equal and/or correlate on a relationship basis with CBT, IBT, BBT, BCT and/or SBT. Moreover, it is suitable if CCT measurements are a perfect match, higher, lower, or not a 1:1 relationship to body temperature.

The disclosed device can offer a practical design that provides means for a comfortable and convenient method of continuously or periodically tracking the wearer's temperature while sleeping. For example, but not limited to, the shape of the device resembles a small, stud earring structure that is wearable on the body, through a wearer's earlobe or a wearer's belly button. This device allows for wireless communication to an external system for tracking continuously or periodically measured CCT, which can be used for the non-limited example of determination of fertility by identifying changes in CCT associated with the biological event of ovulation.

By means of the disclosed device, CCT measurements are obtainable for reliable temperature readings across time. In a non-limiting example, CCT measurements can help assist in the determination of fertility. Within this example, CCT readings are evaluated to differentiate the CCT local minimum during a given night's sleep, where the local minimum is defined by the lowest CCT reading within a pre-established time period. Then local minima can be plotted in relation to time for fertility trends. Additionally, CCT can be tracked over 24 hours and temperatures compared across different days and nights to determine patterns, for a non-limiting example, to identify or predict the wear's date of ovulation.

Traditional fertility thermometers assist in tracking a woman's ovulation trends by measuring her basal body temperature (BBT) through a natural body cavity. These devices do not offer the most accurate ovulation results due to temperature measurements taken after awakening with a non-convenient thermometer. The current device will eliminate the need to awaken before temperature measurements can be taken and more accurately identify the low temperature within a given night's sleep, because the low temperature does not necessarily occur at the time of waking. This will be accomplished by a small, wearable temperature sensor located within an artificial created cavity in the body that offers continuous or periodic readings of CCT.

Figure 1:
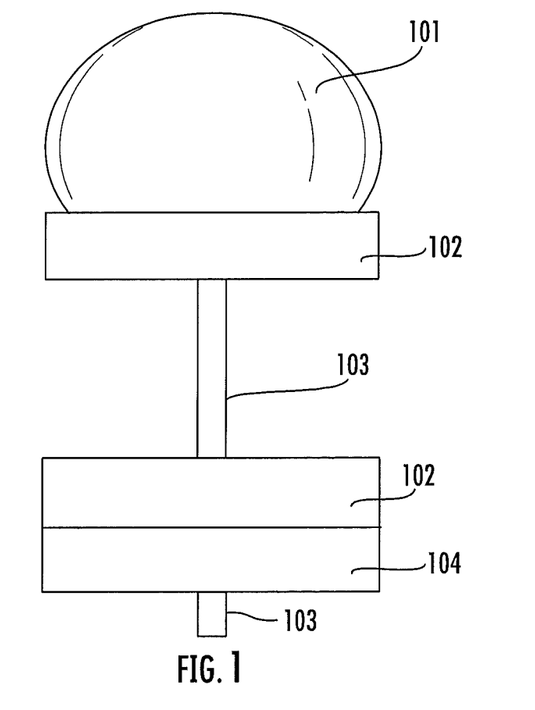
FIG. 1 is a side view of the overall device

Referring to FIG. 1, the present invention includes a multiplicity of individual components to makeup the disclosed device that can be, in a non-limiting example, approximately ¾ inch×¼ inch in total size. The miniature transmitter 101 is attached to the temperature sensor 103, with optional insulating components 102 partially or fully enclosing an artificial cavity when installed in the body. The device may or may not need a miniature battery 104, depending on the type of system.

The miniature transmitter 101 is used for interfacing the temperature sensor to a measurement tracking or control device. For a non-limited example, the shape includes a small, spherical housing, approximately ¼ inch diameter, containing all electrical components needed to operate the temperature sensor 103, in a manner well known in the prior art of electronics. The transmitter is positioned on the distal end of the device and can be connected to an insulating component 102, which are both located outside of the artificial created cavity. The transmitter contains the capability to isolate, amplify, filter noise, linearize, and convert input signals from the temperature sensor 103 and send a standardized output signal to the control device. Common electrical output signals ranges are used.

The optional insulating components 102 can be used to partially or completely close the artificial cavity where the CCT is measured. This component is used to partially or fully enclose the two (entry and exit) ends of the created cavity for more controlled temperature measurement. One insulating component can be permanently located on the distal portion of the device, and a second insulting component can be positioned on the removable proximal portion of the device. The insulting components are made out of a thermal insulating material, a non-limiting example, of which includes synthetic materials such as polyester and polyester blended with other materials such as nylon, spandex or elastin and natural materials such as wool or treated silks, to help control heat loss from the created cavity.

The temperature sensor 103 is a small linear or non-linear rod-like structure, located within and/or through the created artificial cavity, which can be in electronic communication with a circuit board preloaded with operational software for the sensor. The temperature sensor 103 can sense or measure temperature or temperature changes constantly or periodically using specific or nonspecific time intervals. In a non-limiting example, this sensor functions to accurately detect small temperature changes, for measurement orders of about 1 to 0.01 degree Fahrenheit. The temperature sensing means is shown as a unitary sensor unit, although a plurality of sensors can be used. This sensor can optionally operate as a battery-free, wireless sensor node that includes sensors for temperature, humidity, and light, along with an external output.

In this non-limiting example, the optional miniature battery 104 is positioned on the removable, proximal portion of the device, next to the insulating component 102, at the furthest end from the transmitter and outside of the created cavity. This is a low powered battery used to operate the device. In another example, the optional miniature battery is positioned on the non-removable portion of the device.

The miniature battery 104 is not needed when using a receiver as the power source. A development kit can replace the need for a low power battery by converting energy from radio waves (RF energy) into DC power for complete operation of the wireless sensor nodes and other low-power, untethered devices. An example, without limitations, of the receiver includes the Lifetime Power® Energy Harvesting Development Kit for Wireless Sensors, featuring PIC® MCUs with nanoWatt XLP technology. This kit includes continuous power output with roughly an RF range of −5.0 dBm to 20 dBm, configurable output voltage of 1.8V to 4.2V and wireless range of at least 3 meters.

The current device has two parts, including a proximal portion that is able to be disconnected from the distal portion. The distal portion consists of the miniature transmitter 101, optional insulating component 102 and the temperature sensor 103. The removable proximal portion of the device contains an optional insulating component 102 with an option for a miniature battery 104. In an embodiment not shown, the miniature battery is located in the distal portion of the device. The proximal portion is connected to the distal portion by means of the temperature sensor 103, with the proximal portion encompassing the capability to detach by manually sliding off, similar to an earring back. By removing the proximal portion of the device, inserting the distal portion of the device through a created cavity, a non-limiting example of an earring piercing, and returning the proximal portion onto the device, CCT can be measured and tracked.

Figure 2:
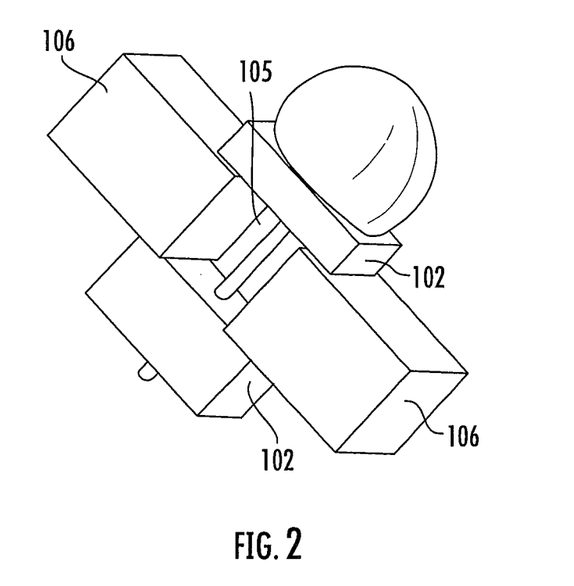
FIG. 2 illustrates the placement of the device within an artificial cavity, which provides an area where temperature is measured

Shown in FIG. 2, the current device is inserted through an artificial created cavity 105, which provides an area for the useful temperature measurement of CCT. The CCT of the created cavity 105 can be measured by the partial or complete closure of a space between the tissue 106 by the insulating components 102, temperature sensor 103, transmitter 101 and/or an earring backing. The artificially created cavity 105 has at least two holes, comprising of at least an entry hole and exit hole for the current device. This created cavity can be a linear or non-linear cavity, as in the non-limiting example of a narrow non-linear tunnel, i.e. belly button piercing. This creates a small bounded area, a non-limiting example of about 1 mm radius and 5 mm length, through the wearer's body for temperature measurements of CCT. A non-limiting example of tissue 106 used for the created cavity is the earlobe, where the insulating components 102, transmitter 101, or an earring backing partially or fully close the hole in the earlobe.

Additionally, two or more artificially created cavities can be utilized for measuring CCT in one body. A non-limiting example, two different temperature sensing devices can be used in two different created cavities to measure two CCT values simultaneously within separate created cavities. Further, these different sensing devices can be used to derive a single CCT.

Figure 3:
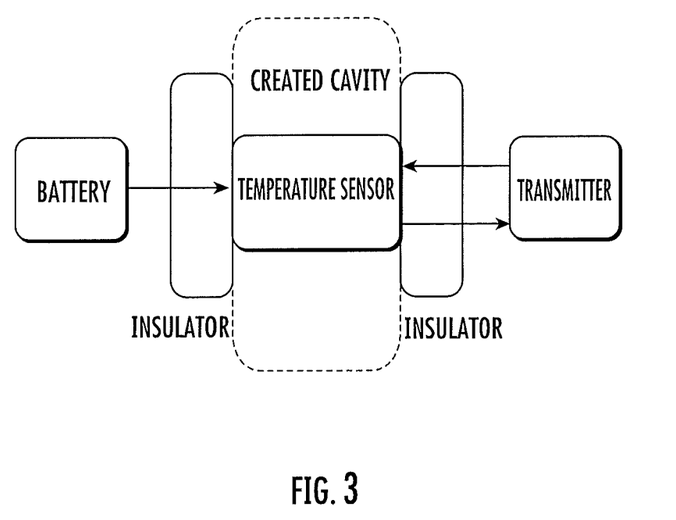
FIG. 3 depicts a block diagram of the device hardware connection in relation to the created cavity FIG. 4 demonstrates a flow chart of the data processing after the device collects temperature data
Figure 4:
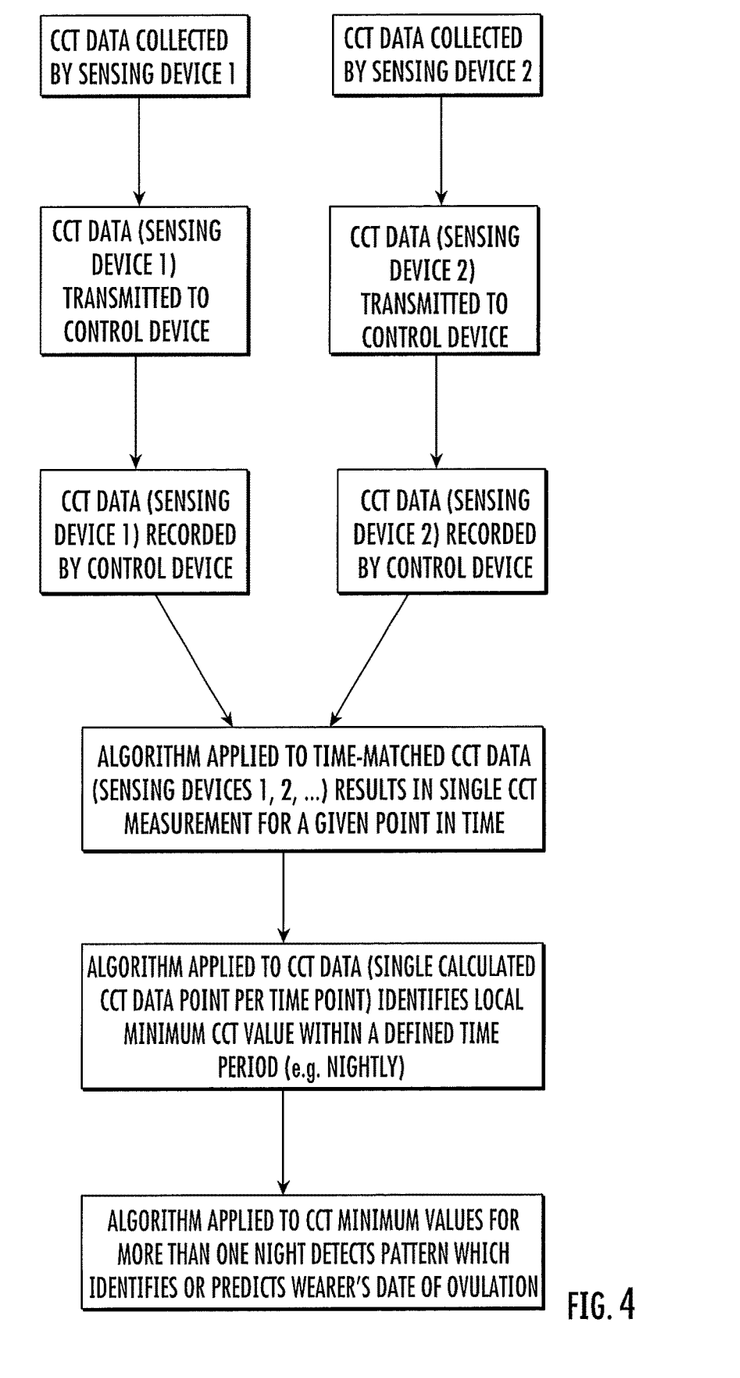

FIG. 3 depicts a diagram of the temperature sensing device hardware connection. As seen in the diagram, a transmitter is connected to the optional first insulating component. The first insulting component is used to partially or fully close the distal end of the created cavity. Within the created cavity, the temperature sensor is connected to the first insulating and second insulting components, where the temperature sensor is the sole device located within the created cavity. The optional second insulating component is used to partially or fully close the proximal end of the created cavity. The second insulating component is connected to an optional battery outside of the created cavity. The battery can be used to power the temperature sensor and/or transmitter. FIG. 4 illustrates a non-limiting flow chart of data processing applied to CCT measurements or values.

Figure 5A:
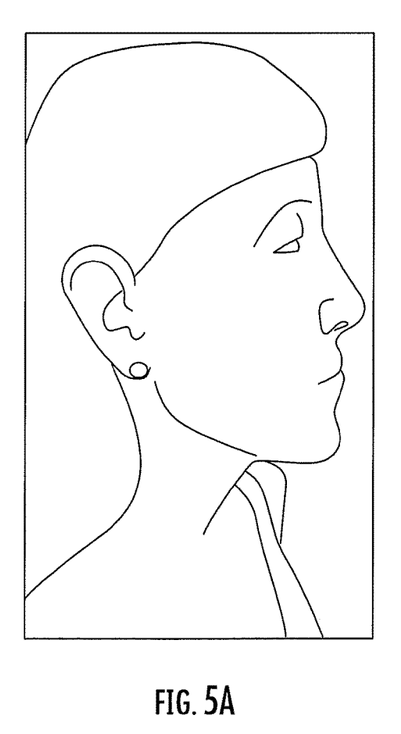
FIG. 5 illustrates a non-limiting example of a woman wearing the device and device embodiments FIG. 6 graphically presents the relationship between tracked temperature values over one month and ovulation prediction.
Figure 5B:
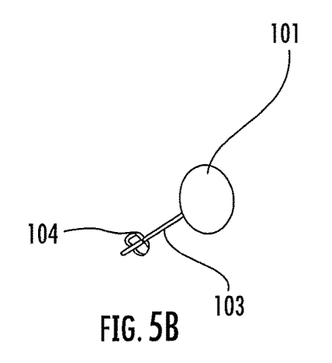
Figure 5C:
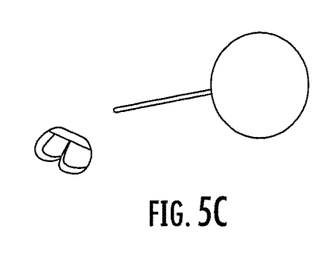

In the non-limiting example, shown in FIG. 5, when common electronics manufacturing techniques are applied to the device, the device can be made to be worn in a manner as simple as wearing an earring. With its small, compact design, this wireless thermometer is intended for continuous wear during normal daily or nightly activities. The size, wearer-friendliness, and non-manual operations allow the wearer to not interrupt daily activities or awaken while the device is reading the wearer's useful temperature of CCT. Further, the CCT information can be wirelessly sent to an external PC or memory device for tracking temperature.

When temperature is sensed, it is transmitted, and then recorded wirelessly to a receiver. The receiver records CCT in a format that retains the CCT value, which sensing device it came from (used to distinguish between different devices when using more than one device at once), and the time. Two or more temperature sensors can be utilized with separate created cavities within one body. When more than one temperature sensor is used at once, the receiver can obtain all temperature readings. These temperatures can be compared and an algorithm can be applied to arrive at one temperature value for that time. For example, but not limited to, one sensing device is used in the left ear with another sensing device used in the right ear. In a non-limiting example, when the receiver obtains both temperature readings, the lowest temperature value is chosen for use in additional calculations.

The recorded temperature values can be plotted against time and an algorithm applied to find local and global minima and maxima. Further, global minima for a given time period can be plotted against sequential time periods.

For example, but not limited to, using the minimum CCT for a given night, which is then implemented across many nights. With applying the algorithm to plot CCT for many nights, quantified patterns are determined and ovulation trends are revealed. One can then draw conclusions derived from ovulation patterns to determine or predict outcomes for physiological consequence and/or state.

The main algorithm is used to determine local and global minima and maxima; although, various optional algorithms can be employed. A non-limiting example of this is seen where an algorithm is used to calculate IBT or BBT by measuring CCT for assistance in determination of fertility.

Figure 6:
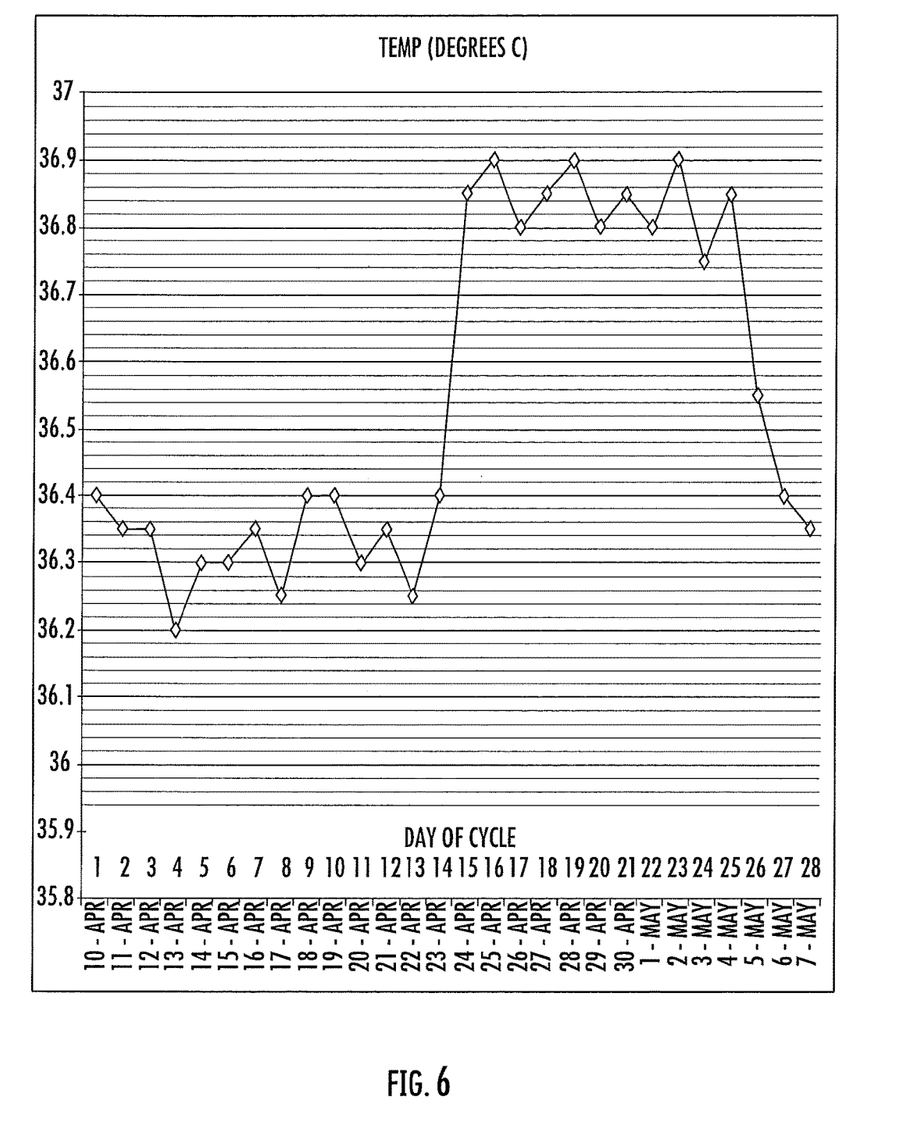

FIG. 6 graphically illustrates the use of temperature measurements in relation to time for determination of fertility. It is known in the art that determining when ovulation occurs can be verified by means of tracking the elevation in body temperature during a woman's fertility cycle, where this temperature rise comes abruptly at the time of ovulation. This temperature rise is caused due to the secretion of progesterone during the latter half of the cycle, which increases the body temperature about one-half degree Fahrenheit. During the first half of the menstrual cycle, the temperature fluctuates around 97.2 to 98.0 degree Fahrenheit, and then in a space of 1-2 days, the temperature undergoes a rather steep rise of about one-half or more degrees Fahrenheit, to around 98.2 to 99.0 degree Fahrenheit. The temperature remains at this higher level until the next menstrual bleeding. With this information, one can extract that, on average, ovulation occurs 1-2 days before the steep rise in temperature. This small increase in temperature explains the need for a temperature sensor that accurately detects small, 0.1 to 0.01 degree Fahrenheit, changes.

The disclosed device is meant for long-lasting use. The materials and electronic components provide strength and capability for continuous wear during the wearer's normal daily activity. If the device provides incorrect readings or other problems, the device maybe disposed by means of the user or manufacturer.

In this disclosure, it is expected that this device will find use to determine fertility. This at-home temperature sensing device is used to draw conclusions derived from patterns about the wearer's physiological consequences and/or state, for example, but not limited to, ovulation, pregnancy, birth control, and/or menstrual cycle. This device also provides capabilities to obtain information based on early detection of one's health issues, like needing to take specific medications or vitamins. This device could also be used for other medical applications, by way of non-limiting example as seen in detection of fever and/or sickness. Further, this device can be used for deriving information for medical tracking and implemented for hospital use in circumstances that require constant or periodic temperature monitoring.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art

Example 1

Figure 7:
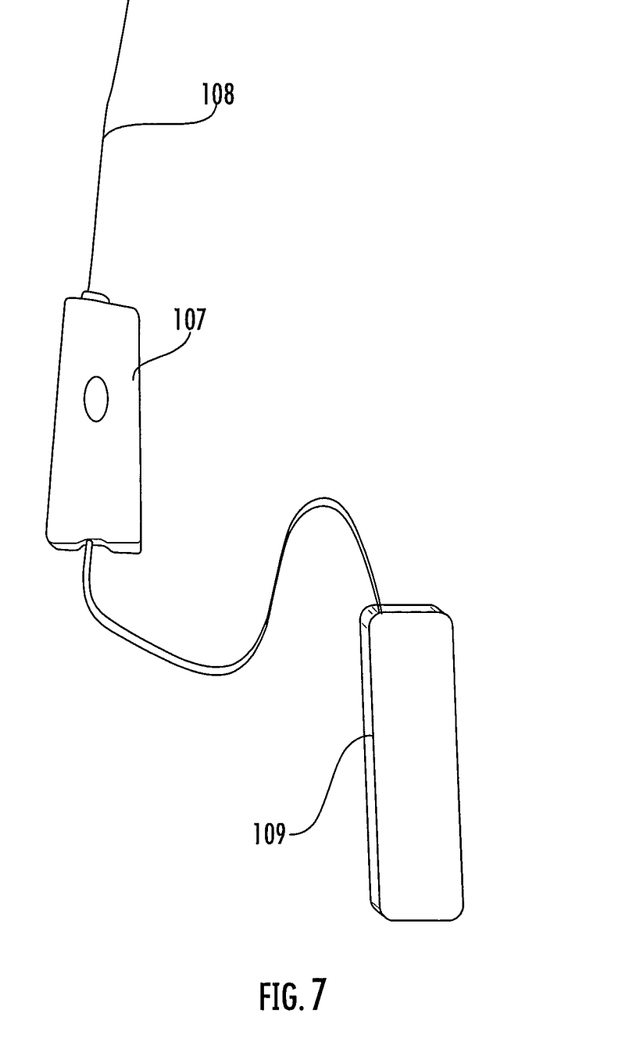
FIG. 7 is a prototype described in Example 1
Figure 8:
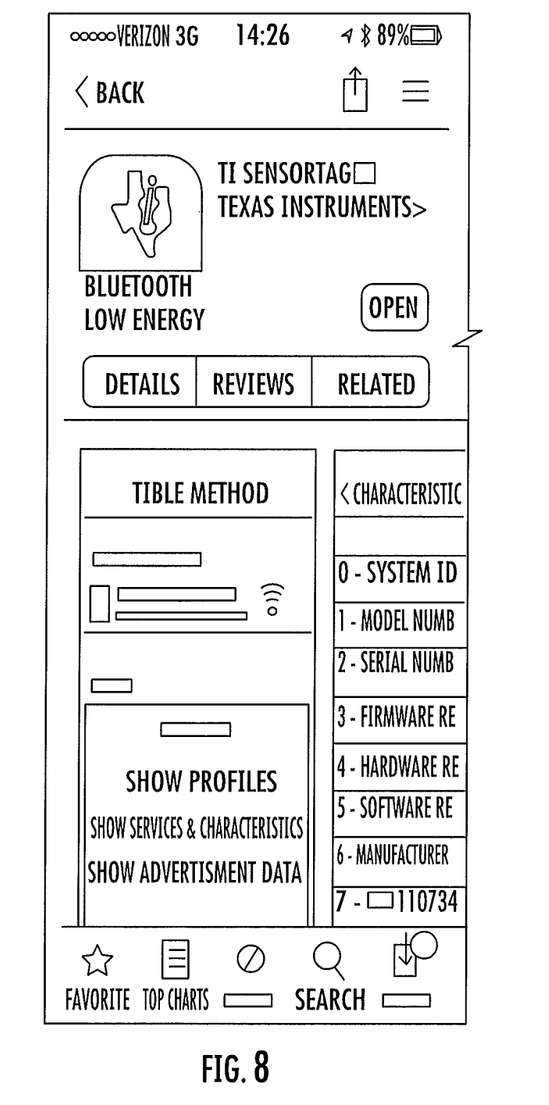
FIG. 8 illustrates the TI Sensor Tag app used to measure temperature in Example 1

Sealevel Systems 9233 Sensor Tag-based prototype was utilized to measure and differentiate ambient temperature and created cavity temperature (CCT). The temperature sensor hardware was designed to model the dimensions of an earring post such as that illustrated in FIG. 7 consists of:
  a. TI SensorTag Bluetooth Smart (Bluetooth Low Energy, BLE) development board 107
  b. Micro NTC thermistor probe, encased in a 21XT gauge Type 304 stainless steel hypodermic tube 108
  c. Sealevel custom SensorTag firmware to read the NTC thermistor and to provide the temperature as a BLE service
  d. A 2×AA battery pack with On/Off switch, powering the SenorTag with 336 hours of estimated battery life 109
  e. iOS-compatible device with Bluetooth capabilities (i.e. iPhone 4s or later, iPad ($3^{rd}$ generation) or later, iPad mini or later, iPod touch ($5^{th}$ generation) or later) is required to connect the SensorTag BLE device (Note: Android-compatible devices with BLE can also be used)

The 9233 Sensor Tag-based prototype was programmed with Sealevel custom firmware, to read the NTC thermistor and to provide temperature as a BLE service. Specifications for the software are as follow:
  a. Firmware supplier: Sealevel Systems, Inc.
  b. Firmware version: 1.5
  c. Thermistor range: [14.99, 60.14] degrees Celsius
  d. Estimated resolution: +/−0.3 degrees Celsius
  e. BLE GATT Spec Health Thermometer (0×1809) compliant
  f. TI SensorTag iOS app by Texas Instruments version 3.5 to connect the SensorTag device and read/log the temperature data (Note: Android TI SensorTag app may also be used)

To log temperature data using the 9233 Sensor Tag-based prototype, the following procedure was used:
  a. On an iOS-compatible device, the SensorTag by Texas Instruments app. as illustrated in FIG. 6 was downloaded and installed on an iOS device.
  b. The iOS device's Bluetooth was turned on, and the SensorTag app was launched
  c. The Sensor Tag-based prototype 2×AA battery pack was switched to ON
  d. In the SensorTag app, the SensorTag device was selected and the connection occurred.
  e. Once connected, the Amibent Temperature service was selected and then the "Show graph" option was selected
  f. The graph displayed the temperate reading, updated once per second. The app was kept open to log the data from the SensorTag-based prototype
  g. The temperature log was sent via email from the SensorTag graph by selecting the lower-left icon (pencil and paper) to a provided email address. The log was provided as an attachment to the email in comma separated value (csv) format.
  h. The SensorTag app was closed to stop logging.

The Sealevel Systems 9233 Sensor Tag-based prototype was used to demonstrate the ability to accurately measure ambient temperature when not mounted in the ear. During testing, the prototype measured a temperature averaging 24.75 deg Celsius. over approximately 5 minutes at a measurement frequency of 1 measurement per second with the earring backing in place and elastic backing in place but not adhered.

Additionally, the Sealevel Systems 9233 Sensor Tag-based prototype was used to explore sensor range. Using the same set-up to measure ambient temperature, the prototype measured temperature to demonstrate reception of signal from 25 feet from an iPhone, including receiving signal through the human body (torso) and sheetrock walls. The prototype measured temperature averaging 24.88 deg Celsius. over approximately 15 minutes (1 measurement per second) with no interruptions when the receiver moved out to 25 feet with periodic intervening bodies or walls between the receiver and transmitter.

To measure CCT, the Sealevel Systems 9233 Sensor Tag-based prototype was used in an artificially created cavity in the ear lobe. The hollowed created cavity was partially closed using an insulating backing on one side of the ear lobe and an earring backing on the other. The prototype measured the created cavity temperature averaging 36.93 deg Celsius. over approximately 2 minutes at a measurement frequency of 1 measurement per second.

This experiment demonstrated the Sealevel Systems 9233 Sensor Tag-based prototype has the ability to measure and differentiate ambient temperature and created cavity temperature over time. The measured ambient temperature corresponded to the room temperature during the measurement time as measured by a common household thermostat. The measured created cavity temperature was higher than ambient temperature during its measurement time. As well, the sensor was able to measure temperature when the receiver and sensor were 25 feet apart with periodic intervening bodies or walls between the receiver and transmitter.

What is claimed is:

1. An earring configured for insertion and being worn in an artificially-created human ear tissue cavity bounded by a first hole in the ear tissue and a second hole in the ear tissue opposite the first hole, the earring consisting of:
   an earring post;
   said earring post comprising an electronic temperature sensor;
   said earring post being dimensioned to be inserted through at least the first hole of the ear tissue and into the artificially-created ear tissue cavity;
   said electronic temperature sensor being configured, upon said earring post being inserted into the artificially-created ear tissue cavity, to provide a temperature measurement of the temperature within the artificially-created ear tissue cavity;
   an electronic transmitter configured to wirelessly transmit said temperature measurement; and
   at least one power supply that powers said electronic temperature sensor and said electronic transmitter, wherein the power supply harvests energy from radio waves, Wi-Fi signals, or other signals and/or includes a battery.

2. An earring configured for insertion and being worn in an artificially-created human ear tissue cavity bounded by a first hole in ear tissue and a second hole in ear tissue opposite the first hole, the earring consisting of:
   an earring post;
   said earring post comprising an electronic temperature sensor;
   said earring post being dimensioned to be inserted through at least the first hole of the ear tissue and into the artificially-created ear tissue cavity;
   said electronic temperature sensor being configured, upon said earring post being inserted into the artificially-created ear tissue cavity, to provide a temperature measurement of the temperature within the artificially-created ear tissue cavity;
   an electronic transmitter configured to wirelessly transmit said temperature measurement;
   at least one power supply that powers said electronic temperature sensor and said electronic transmitter, wherein the power supply harvests energy from radio waves, Wi-Fi signals, or other signals and/or includes a battery; and
   at least one selected from the group consisting of a closure and at least one insulator configured to partially or completely enclose at least one of the first hole and the second hole of the artificially-created ear tissue cavity.

3. The earring of claim 1, wherein the temperature sensing occurs intermittently, periodically using specified time intervals, or substantially continuously.

4. The earring of claim 2, wherein the temperature sensing occurs intermittently, periodically using specified time intervals, or substantially continuously.

5. A belly button ring configured for insertion and being worn in an artificially-created human belly button tissue cavity bounded by a first hole in belly button tissue and a second hole in belly button tissue opposite the first hole, the belly button ring consisting of:
   a belly button ring post;
   said belly button ring post comprising an electronic temperature sensor;
   said belly button ring post being dimensioned to be inserted through at least the first hole of the ear tissue and into the artificially-created belly button tissue cavity;
   said electronic temperature sensor being configured, upon said belly button ring post being inserted into the artificially-created belly button tissue cavity, to provide a temperature measurement of the temperature within the artificially-created belly button tissue cavity;
   an electronic transmitter configured to wirelessly transmit said temperature measurement; and
   at least one power supply that powers said electronic temperature sensor and said electronic transmitter, wherein the power supply is at least one of a battery and a power supply that harvests energy from radio waves, Wi-Fi signals, or other signals.

6. A belly button ring configured for insertion and being worn in an artificially-created human belly button tissue cavity bounded by a first hole in belly button tissue and a second hole in belly button tissue opposite the first hole, the belly button ring consisting of:
   a belly button ring post;
   said belly button ring post comprising an electronic temperature sensor;
   said belly button ring post being dimensioned to be inserted through at least the first hole of the ear tissue and into the artificially-created belly button tissue cavity;
   said electronic temperature sensor being configured, upon said belly button ring post being inserted into the artificially-created belly button tissue cavity, to provide a temperature measurement of the temperature within the artificially-created belly button tissue cavity;
   an electronic transmitter configured to wirelessly transmit said temperature measurement;
   at least one power supply that powers said electronic temperature sensor and said electronic transmitter, wherein the power supply is at least one of a battery and a power supply that harvests energy from radio waves, Wi-Fi signals, or other signals; and
   at least one selected from the group consisting of a closure and at least one insulator configured to partially or completely enclose at least one of the first hole and the second hole of the artificially-created belly button tissue cavity.

7. The belly button ring of claim 5, wherein the temperature sensing occurs intermittently, periodically using specified time intervals, or substantially continuously.

8. The belly button ring of claim 6, wherein the temperature sensing occurs intermittently, periodically using specified time intervals, or substantially continuously.

* * * * *

UNITED STATES PATENT AND TRADEMARK OFFICE
CERTIFICATE OF CORRECTION

| | | |
|---|---|---|
| PATENT NO. | : 10,117,643 B2 | Page 1 of 1 |
| APPLICATION NO. | : 14/696395 | |
| DATED | : November 6, 2018 | |
| INVENTOR(S) | : Theresa Anne Gevaert and Matthew Raymond Gevaert | |

It is certified that error appears in the above-identified patent and that said Letters Patent is hereby corrected as shown below:

On the Title Page

Add the following priority claim:
Related U.S. Application Data
(60) Provisional application No. 61/984,732, filed on April 26, 2014.

Signed and Sealed this
Sixth Day of May, 2025

Coke Morgan Stewart
*Acting Director of the United States Patent and Trademark Office*